United States Patent [19]
Ozlen

[11] Patent Number: 5,441,740
[45] Date of Patent: Aug. 15, 1995

[54] COSMETIC COMPOSITION CONTAINING ALPHA HYDROXYACIDS, SALICYCLIC ACID, AND ENZYME MIXTURE OF BROMELAIN AND PAPAIN

[75] Inventor: Susan N. Ozlen, Chatsworth, Calif.

[73] Assignee: Longevity Network. Ltd., Henderson, Nev.

[21] Appl. No.: 238,816

[22] Filed: May 6, 1994

[51] Int. Cl.⁶ .............................................. A61K 7/48
[52] U.S. Cl. .................................. 424/401; 424/942; 514/844; 514/846; 514/859; 514/944
[58] Field of Search ................ 424/401, 942; 514/844, 514/846, 859, 944

[56] References Cited

U.S. PATENT DOCUMENTS 5,091,171  2/1992  Yu et al. ............................... 424/642

OTHER PUBLICATIONS

JP 238539 (1989) Abstract.

*Primary Examiner*—Jyothsna Denkat

[57] ABSTRACT

Compositions containing at least one alpha hydroxyacid, salicylic acid, and at least one digestive enzyme derived from fruit are disclosed for cosmetic uses in the treatment of various skin conditions such as lack of adequate skin firmness, wrinkles, and dry skin. Various formulations of the compositions including gels, creams, lotions and ointments are disclosed for topical use. The alpha hydroxyacids include glycolic acid, lactic acid and citric acid. The digestive enzymes include bromelain and papain.

10 Claims, No Drawings

COSMETIC COMPOSITION CONTAINING ALPHA HYDROXYACIDS, SALICYCLIC ACID, AND ENZYME MIXTURE OF BROMELAIN AND PAPAIN

BACKGROUND OF THE INVENTION

1. Field of the Invention

This invention relates to cosmetic compositions, and more particularly to such compositions containing alpha hydroxyacids, salicylic acid, and digestive enzymes.

2. Background

Skin problems range between severe skin disorders such as eczema, psoriasis and the like, and less severe skin conditions, such as wrinkles, acne and dry skin.

In the past, treatment has included various compositions containing a wide variety of active ingredients such as organic and inorganic acids, steroids, fungicides, antibiotics and anti-inflammatory substances.

U.S. Pat. No. 5,276,061 describes cosmetic compositions containing 1 alpha-hydroxyvitamin D homolog compounds for treatment of various skin conditions.

U.S. Pat. No. 5,091,171 describes amphoteric compositions containing alpha hydroxyacids, alpha ketoacids, related compounds or polymeric forms of hydroxyacids for treatment to alleviate cosmetic conditions and symptoms of dermatologic disorders.

U.S. Pat. No. 4,824,865 describes a method for treatment of the skin disorder of tinea pedis in man and other mammals with a composition containing the organic acids, 2-hydroxyoctanoic acid, 2-ketooctanoic acid, and certain esters thereof.

U.S. Pat. No. 4,380,549 describes a method for alleviating symptoms of dry skin comprising applying a composition containing one or more hydroxy acids or analogues of hydroxy acids.

Although some relief from at least some of the skin disorders has been possible following treatment, complete remission has not always been possible, nor is there any evidence that long term freedom from the symptoms of the skin disorders has been experienced when employing the compounds which are the subject of these prior proposals.

SUMMARY OF THE INVENTION

It has now been found that compositions comprising alpha hydroxyacids, salicylic acid and digestive enzymes are effective when topically applied to prevent as well as help alleviate various skin conditions including wrinkles and dry skin.

The present invention then relates to cosmetic compositions comprising at least one alpha hydroxyacid, salicylic acid, and at least one digestive enzyme derived from a fruit extract. The alpha hydroxy acids include, but are not limited to, glycolic, citric, malic and lactic acids. The at least one alpha hydroxyacid is present in an amount of about 5 weight %, the salicylic acid is present in an amount of about 1 weight %, and the at least one digestive enzyme is present in an amount of about 0.20 weight %.

In a preferred embodiment of the composition, the at least one alpha hydroxyacid is a mixture of glycolic, lactic and citric acids and the at least one digestive enzyme is a mixture of bromelain and papain.

In a more preferred embodiment of the composition, the glycolic and citric acids are each present in an amount of about 2 weight %, the lactic acid is present in an amount of about 1 weight %, the salicylic acid is present in an amount of about 1 weight %, the bromelain is present in an amount of about 0.10 weight %, and the papain is present in an amount of about 0.10 weight %. The citric acids are preferably derived from grapefruit and passion fruit extracts.

The present invention also relates to methods for alleviating the symptoms of skin conditions such as dry skin with a nontoxic solution, gel, lotion, cream or ointment of a composition containing alpha hydroxyacids, salicylic acid and digestive enzymes. The method comprises applying to involved areas of the body an effective amount of a composition comprising alpha hydroxyacids, salicylic acid and digestive enzymes.

Various formulations for the cosmetic compositions are disclosed. The compositions of this invention are formulated preferably as solutions, gels, creams, lotions, ointments and the like by choice of appropriate carriers. Suitable carriers include deionized water, vegetable or mineral oils, white petrolatum, branched chain fats or oils, animal fats and high molecular weight alcohol. The preferred carriers are those in which the active ingredients are soluble. Emulsifiers, stabilizers and antioxidants may also be included as well as agents imparting color or fragrance. The efficacious ingredients, including the alpha hydroxy acids and fruit enzymes, are best added to the formulation at temperatures below 40° C.

The compositions disclosed herein unexpectedly provide highly effective treatments for various skin conditions without producing unwanted systemic or local side effects.

Other features and advantages of the present invention will become apparent from the following more detailed description.

DETAILED DESCRIPTION OF THE INVENTION

It has now been found that effective treatment of various skin conditions can be achieved with compositions which include alpha hydroxyacids, salicylic acid, and digestive enzymes.

Compositions according to the present invention comprise: at least one alpha hydroxyacid, salicylic acid, and at least one digestive enzyme derived from a fruit extract.

As used in the description, and in the claims, the term "alpha hydroxyacid" refers to compounds represented by the following generic structure:

$$(R_1)(R_2)C(OH)COOH$$

where $R_1$ and $R_2$ are H, alkyl, aralkyl or aryl groups. In addition, $R_1$ and $R_2$ may carry OH, CHO, COOH and alkoxy groups. Typical alkyl, aralkyl and aryl groups for $R_1$ and $R_2$ include methyl, ethyl, propyl, isopropyl, butyl, pentyl, octyl, lauryl, stearyl, benzyl and phenyl etc. The alpha hydroxy acids include, but are not limited to, glycolic, lactic, malic and citric acids.

The at least one alpha hydroxyacid is preferably a mixture of glycolic, lactic and citric acids. The at least one digestive enzyme derived from fruit is preferably a mixture of bromelain and papain.

Bromelain is a protein-digesting enzyme found in pineapple. It is typically obtained from pineapple Juice by precipitation with acetone and also with ammonium sulfide. Papain is a protein-digesting enzyme found in the fruit and leaves of papaya. Papain is typically obtained from dried papaya latex.

The composition of the invention can be prepared in the form of a solution, lotion, gel, cream, or ointment suited to topical administration.

When the composition is a liquid, such as a solution, lotion, gel, cream or ointment, then it is usually necessary to dissolve the alpha hydroxyacids, salicylic acid, and digestive enzymes in water or alcohol or other aqueous and non-aqueous pharmaceutically acceptable vehicle, and then to admix this solution, if desired, in a conventional manner with a suitable gel, cream, lotion, or ointment base in order to prepare the pharmaceutical composition.

Suitable carriers include deionized water, vegetable or mineral oils, white petrolatum, branched chain fats or oils, animal fats and high molecular weight alcohol. The preferred carriers are those in which the active ingredients are soluble. Emulsifiers, stabilizers and antioxidants may also be included as well as agents imparting color or fragrance.

The amount of alpha hydroxyacids, salicylic acid, and digestive enzymes will depend on the nature of the composition. However, it can be stated generally that the amount of these active ingredients will be present in the following amounts: the alpha hydroxyacids are present in an amount of about 5 weight %, the salicylic acid is present in an amount of about 1 weight percent, and the digestive enzymes are present in an amount of about 0.20 weight %.

In a preferred embodiment, the at least one alpha hydroxyacid is a mixture of glycolic, lactic, and citric acids and the digestive enzymes derived from fruit are bromelain and papain. The glycolic and citric acids are each present in an amount of about 2 weight %, and the lactic acid is present in an amount of about 1 weight %, the salicylic acid is present in an amount of about 1 weight %, the bromelain is present in an amount of about 0.10 weight %, and the papain is present in an amount of about 0.10 weight %. The citric acids are preferably derived from grapefruit and passion fruit extracts.

The method according to the invention comprises the steps of applying to involved areas of the body an effective amount of a composition comprising alpha hydroxyacids, salicylic acid and digestive enzymes derived from fruit.

The following example illustrates a formulation according to the present invention.

EXAMPLE 1

| INGREDIENTS | % w/w |
| --- | --- |
| Deionized Water | 68.95 |
| Alpha hydroxyacids | 5.00 |
| Salicylic acid | 1.00 |
| Capric/Caprylic Triglycerides | 5.00 |
| Stearic Acid | 4.00 |
| c12-15 Alkyl Benzoate | 4.00 |
| Glyceryl Stearate (and) PEG-100 Stearate | 2.00 |
| Isopropyl Palmitate | 2.00 |
| Propylene Glycol | 2.00 |
| Cetyl Alcohol | 1.00 |
| Sorbitan Stearate | 1.00 |
| Stearamidopropyl Dimethylamine | 0.50 |
| Stearyl Alcohol | 0.50 |
| Tocopheryl Acetate | 0.10 |
| Tocopheryl Linoleate | 0.10 |
| Ascorbyl Palmitate | 0.10 |
| Retinyl Palmitate | 0.05 |
| Panthenol | 0.10 |
| Beta-Carotene | 0.05 |
| Superoxide Dismutase | 0.05 |
| Gingko Biloba | 0.05 |
| Carnosine | 0.05 |
| Phoroglucinol | 0.05 |
| Selenium | 0.01 |
| Zinc | 0.01 |
| Copper | 0.01 |
| Bromelain | 0.10 |
| Papain | 0.10 |
| Borage Oil | 0.01 |
| Evening Primrose Oil | 0.01 |
| Hydroxethylcellulose | 0.50 |
| Dimethicone | 0.50 |
| Disodium Edta | 0.05 |
| Sodium Hydroxide | 0.50 |
| Methylparaben | 0.20 |
| Propylparaben | 0.10 |
| Imidazolidinyl Urea | 0.20 |
| Fragrance | 0.05 |

The compositions disclosed herein unexpectedly provide highly effective treatments for various skin conditions without producing unwanted systemic or local side effects.

The papain and bromelain work synergistically to gently lift and remove older, upper layers of skin, revealing the fresher, younger skin cells beneath. The combination of alpha hydroxyacids and salicylic acid function to loosen the "glue" holding skin cells together, allowing them to be gently sloughed off consistently and readily, helping to prevent the sloughing off of "clumped" skin cells, which is observed as flaking and dry, patchy skin. Papaya and pineapple enzymes, i.e., bromelain and papain, gently "digest" the protein in skin cells refining coarse, thickened skin for a smoother textured appearance.

This dual action approach gives more effective exfoliating results while maintaining the mildness of the combination of alpha hydroxyacids and salicylic acid of the invention in comparison to prescription drugs, such as Retin-A, that can reduce superficial wrinkles.

The cosmetic benefits of the composition of the present invention are improved skin tone, due to greater translucency (older, more opaque skin cells are removed), softer, smoother skin, fading of age spots, diminished fine lines and wrinkles and a finer, improved texture and appearance attributed to the exposure of the underlying layers of the skin.

In addition to the exfoliating benefits of the composition, other advantages are that use of the product does not increase sensitivity to the sun, helps increase skin's elasticity and moisture retention, may help increase skin's production of the natural humectant, hyaluronic acid, and is suitable for all skin types.

The composition of the present invention produces more noticeable results in a shorter period of time in comparison to products containing the same levels of alpha-hydroxy acids without enzymes. This allows enhanced results to be achieved, while maintaining mildness by not increasing the alpha hydroxyacid levels of the products.

The foregoing detailed description has been directed to particular embodiments of the invention for the purposes of illustration and explanation. It will be apparent, however, to those skilled in this art that modifications and changes in the compositions and processes set forth will be possible without departing from the scope and spirit of the invention.

What is claimed is:

1. A composition for topical treatment of cosmetic conditions or dermatologic disorders which comprises an effective amount of at least one alpha hydroxyacid, salicylic acid, and at least one digestive enzyme derived from fruit in a cosmetically acceptable topical carrier for said composition;
   wherein said at least one alpha hydroxyacid comprises mixture of glycolic, lactic and citric acids, and
   wherein said at least one digestive enzyme is a mixture of bromelain and papain; and
   wherein said alpha hydroxyacid is present in an amount of about 5 weight %, said salicylic acid is present in an amount of about 1 weight %, and said digestive enzyme is present in an amount of about 0.20 weight %.

2. A composition for topical treatment of cosmetic conditions or dermatologic disorders which comprises an effective amount of at least one alpha hydroxyacid, salicylic acid, and at least one digestive enzyme derived from fruit in a cosmetically acceptable topical carrier for said composition;
   wherein said at least one alpha hydroxyacid comprises a mixture of glycolic, lactic and citric acids, and
   wherein said at least one digestive enzyme is a mixture of bromelain and papain; and
   wherein said glycolic and citric acids are each present in an amount of about 2 weight %, said lactic acid is present in an amount of about 1 weight %, said salicylic acid is present in an amount of about 1 weight %, said bromelain is present in an amount of about 0.10 weight %, and said papain is present in an amount of about 0.10 weight %.

3. A composition according to claim 2 wherein said citric acid is derived from one or more fruits selected from the group consisting of grapefruit and passion fruit.

4. A composition according to claim 2 wherein the composition is in the form of a gel, cream, lotion or ointment.

5. A composition according to claim 4 wherein the cosmetically acceptable topical carrier includes deionized water present in an amount of about 69 weight % of said composition.

6. A method for treating the skin conditions of skin slackness, wrinkles, and dry skin which comprises topically applying to involved areas of the human body an effective amount of a composition comprising at least one alpha hydroxyacid, salicylic acid, and at least one digestive enzyme derived from fruit in a cosmetically acceptable topical carrier for said composition
   wherein said at least one alpha hydroxyacid is a mixture of glycolic, lactic and citric acids; and
   wherein said at least one digestive enzyme is a mixture of bromelain and papain; and
   wherein said alpha hydroxyacid is present in an amount of about 5 weight %, said salicylic acid is present in an amount of about 1 weight %, and said digestive enzyme is present in an amount of about 0.20 weight %.

7. A method for treating the skin conditions of skin slackness, wrinkles, and dry skin which comprises topically applying to involved areas of the human body an effective amount of a composition comprising at least one alpha hydroxyacid, salicylic acid, and at least one digestive enzyme derived from fruit in a cosmetically acceptable topical carrier for said composition
   wherein said at least one alpha hydroxyacid is a mixture of glycolic, lactic and citric acids; and
   wherein said at least one digestive enzyme is a mixture of bromelain and papain; and
   wherein said glycolic and citric acids are each present in an amount of about 2 weight %, said lactic acid is present in an amount of about 1 weight %, said salicylic acid is present in an amount of about 1 weight %, said bromelain is present in an amount of about 0.10 weight %, and said papain is present in an amount of about 0.10 weight %.

8. A method according to claim 7 wherein said citric acid is derived from one or more fruits selected from the group consisting of grapefruit and passion fruit.

9. A method according to claim 7 wherein said composition is in the form of a gel, cream, lotion or ointment.

10. A method according to claim 9 wherein said cosmetically acceptable topical carrier includes deionized water present in an amount of about 69 weight % of said composition.

* * * * *